(12) United States Patent
Guo et al.

(10) Patent No.: US 8,968,763 B2
(45) Date of Patent: *Mar. 3, 2015

(54) BLOCK BIODEGRADABLE COPOLYMERS FOR MEDICAL DEVICES

(75) Inventors: Ya Guo, Cotati, CA (US); Peiwen Cheng, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 833 days.

This patent is subject to a terminal disclaimer.

(21) Appl. No.: 12/708,633

(22) Filed: Feb. 19, 2010

(65) Prior Publication Data

US 2010/0158981 A1  Jun. 24, 2010

Related U.S. Application Data

(62) Division of application No. 11/556,865, filed on Nov. 6, 2006, now Pat. No. 7,691,402.

(51) Int. Cl.
| | |
|---|---|
| A61F 2/00 | (2006.01) |
| A61K 31/436 | (2006.01) |
| A61K 31/56 | (2006.01) |
| A61K 31/66 | (2006.01) |
| A61K 31/7052 | (2006.01) |
| A61K 33/00 | (2006.01) |
| A61K 39/395 | (2006.01) |
| A61P 37/06 | (2006.01) |
| A61P 43/00 | (2006.01) |
| A61L 31/06 | (2006.01) |
| A61L 31/10 | (2006.01) |
| A61L 31/16 | (2006.01) |

(52) U.S. Cl.
CPC ............ *A61L 31/06* (2013.01); *A61L 31/10* (2013.01); *A61L 31/16* (2013.01); *A61L 2300/416* (2013.01)
USPC ........ 424/426; 424/718; 424/130.1; 514/182; 514/108; 514/291

(58) Field of Classification Search
CPC ......... A61L 31/06; A61L 31/10; A61L 31/16; A61L 2300/416; C08L 75/04; C08L 67/04
USPC ............... 424/426, 130.1, 718; 514/108, 182, 514/291, 44 A, 44 R
See application file for complete search history.

(56) References Cited

U.S. PATENT DOCUMENTS

| | | | | |
|---|---|---|---|---|
| 4,057,537 | A | * | 11/1977 | Sinclair .................... 528/354 |
| 5,362,718 | A | | 11/1994 | Skotnicki et al. |
| 5,560,973 | A | | 10/1996 | Hoyt et al. |
| 5,716,981 | A | | 2/1998 | Hunter et al. |
| 6,015,815 | A | | 1/2000 | Mollison |
| 6,153,252 | A | * | 11/2000 | Hossainy et al. .............. 427/2.3 |
| 6,329,386 | B1 | | 12/2001 | Mollison |
| 6,338,739 | B1 | | 1/2002 | Datta et al. |
| 6,855,770 | B2 | | 2/2005 | Pinchuk et al. |
| 2003/0139567 | A1 | | 7/2003 | Kim et al. |
| 2005/0112170 | A1 | | 5/2005 | Hossainy et al. |
| 2005/0147647 | A1 | | 7/2005 | Glauser et al. |

FOREIGN PATENT DOCUMENTS

| | | |
|---|---|---|
| WO | WO99/10404 | 3/1999 |
| WO | WO03/090807 | 11/2003 |

OTHER PUBLICATIONS

Cohn, Biomaterials, 26, 2005.*
Drachman, Neointimal Thickening After Stent Delivery of Paclitaxel : Change in Composition and Arrest of Growth Over Six Months.

* cited by examiner

*Primary Examiner* — Susan Tran
*Assistant Examiner* — William Craigo

(57) ABSTRACT

Disclosed herein are implantable medical devices comprising controlled release biodegradable block copolymers or coated with controlled release block copolymers and at least one drug releasable from the block copolymer. The controlled release block copolymers comprise least two blocks selected from the group consisting of polyesters, polyethers, and polyurethanes.

14 Claims, No Drawings

BLOCK BIODEGRADABLE COPOLYMERS FOR MEDICAL DEVICES

RELATED APPLICATIONS

This application is a Division of and claims the benefit of U.S. patent application Ser. No. 11/556,865 filed Nov. 6, 2006.

FIELD OF THE INVENTION

The present invention relates to medical devices comprise of or coated with block copolymers.

BACKGROUND OF THE INVENTION

Recently, highly biocompatible polymers have been formulated to provide implantable medical devices with coatings. These coatings not only increase an implant's tissue compatibility but can also function as bioactive agent reservoirs. However, designing polymer coatings for medical devices has proven problematic. Medical device coatings must be non-toxic, durable and adhere well to device surfaces. Additionally, when the medical device comes into intimate contact with tissues such as blood and internal organs it must also be biocompatible. Furthermore, if the medical device is designed to be pliable either in operation or deployment, the coating must resist cracking, fracture and delamination.

Moreover, polymer coatings on medical devices intended to act as bioactive agent (drug) eluting devices must not only be biocompatible, structurally stable, resistant to delamination, but also chemically compatible with the drug to be administered. Furthermore, if the coating is also intended to control the drug's release rate into adjacent tissue the polymer used must possess other highly specialized properties as well such as, but not limited to appropriate glass transition temperatures and appropriate hydrophilicity/hydrophobicity indexes.

One of the most widely used techniques to modify the properties of a polymer material is to blend different polymers or copolymers together into a single mixture. The resulting polymer mixtures possess a combination of properties of each polymer or copolymer component of the blend. Not all polymers, however, are miscible and thus instead of forming a uniform blend, the polymers can form immiscible mixtures subject to phase separation and delamination. When used as coatings for medical devices this problem becomes even more pronounced. One polymer component may have a stronger affinity for the medical device surface than another and thus may layer closer to the medical device surface. The polymer component having less affinity and avidity for the medical device surface migrates away from the medical device surface resulting in a bi-layer where each polymer component retains its individual properties and the coating no longer functions as a cohesive uniform substance. When bioactive agents are included in the mixture, the problems associated with immiscibility are magnified by the addition of yet a third chemical species having unique chemical properties. An additional variable is introduced by the material of the medical device substrate.

Thus, prior art methods used to develop polymer coatings, specifically drug-eluting coatings, have been largely by trial and error. Recently, the present inventors have developed methods for reducing uncertainty in coating design by matching polymer components with bioactive agents based, in part, on solubility factors. While these procedures have significantly advanced polymer coating science, the primary focus of this disclosure is directed at polymer block copolymers.

Block copolymers are important polymer compositions for use as medical device coatings and as drug-eluting reservoirs as well as fabricating medical devices. Block copolymers are copolymers having individual subunits integrated into a single macromolecule. Different compositions in the polymers will yield different physical properties that can be advantageous to various medical applications. Consequently these are stable compounds not prone to delaminate or separate. Moreover, pendent R groups present within each block can be modified to increase or decrease overall polymer miscibility with bioactive agents without adversely affecting the polymer's structural performance characteristics. Unfortunately, block copolymers are very difficult to synthesize and thus, to date, there are only a limited number of polymers commercially available for medical use. Recent advances in synthetic chemistry, however, have led to the development of new methods for free radical polymerization; specifically atom transfer radical polymerization (ATRP) and reversible addition-fragmentation chain transfer (RAFT). These new synthetic methods can provide for the convenient synthesis of a wide range of block copolymers that were previously impossible or difficult to make.

U.S. Pat. No. 6,855,770 B2 (hereinafter the '770 patent) issued Feb. 15, 2005 to Pinchuck et al. describe certain medical grade block copolymers useful for drug delivery. The '770 patent discloses a block copolymer comprising one or more elastomeric blocks and one or more thermoplastic blocks combined with a therapeutic agent, specifically a polystyrene-polyisobutylene-polystyrene copolymer combined with paclitaxel and used to coat a vascular stent. The block copolymers in the '770 patent are made using carbocationic polymerization (living ionic polymerization) and synthesis is conducted under conditions that minimize or avoid chain transfer termination of the growing chain. However, these prior art methods are very susceptible to attack, and thus termination, by active hydrogens; consequently water, alcohol and the like must be kept to a minimum. This limitation in prior art methods significantly limits the range of solvents and hydrocarbons that can be used. These limited reaction conditions and monomer subunit selections leads to a narrow range of polymer types and thus restricted compatibility with diverse bioactive agents.

Thus, there is a need for improved polymeric materials suitable for coating implantable medical devices. Therefore, it is an object of the present invention to provide compositions and associated methods for a wide range of biocompatible block copolymers, useful for coating and forming implantable medical devices.

SUMMARY OF THE INVENTION

The present invention provides controlled release biodegradable block copolymers for fabricating and coating medical devices. In particular, controlled release biodegradable block copolymers made in accordance with the teachings of the present invention are suitable for coating and fabricating vascular stents. The block copolymers can be customized to deliver bioactive agents including, but not limited to, hydrophilic or hydrophobic drugs and large molecules such as proteins or DNA.

In one embodiment of the present invention, an implantable medical device is provided comprising a controlled release biodegradable block copolymer comprising at least two blocks selected from the group consisting of polyesters, polyethers, and polyurethanes and at least one drug releasable from said block copolymer. In another embodiment, a medical device is provided having a coating comprising a biodegradable block copolymer having at least two blocks selected from the group consisting of polyesters, polyethers, and polyurethanes and at least one drug releasable from said block copolymer. In another embodiment, the block copolymer comprises monomers selected from the group consisting of ε-caprolactone, cyclohexyl caprolactone, polyethylene glycol, 1,8 octanediol, trimethylene carbonate, lactide, glycolide, and their derivatives.

In another embodiment of the present invention, the medical device is a vascular stent.

In an embodiment of the present invention, the block copolymer comprises the general structure of Formula 6;

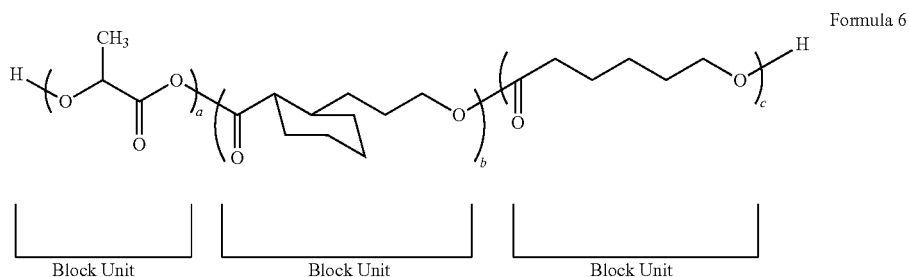

Formula 6 wherein a is an integer from about 2 to about 30,000, b is an integer from about 2 to about 30,000, and c is an integer from about 2 to about 30,000.

In another embodiment of the present invention, the block copolymer comprises the general structure of Formula 7;

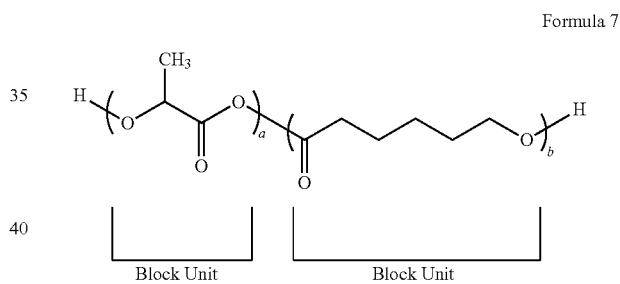

Formula 7 wherein a is an integer from about 2 to about 30,000 and b is an integer from about 2 to about 30,000.

In another embodiment of the present invention, the block copolymer comprises the general structure of Formula 8;

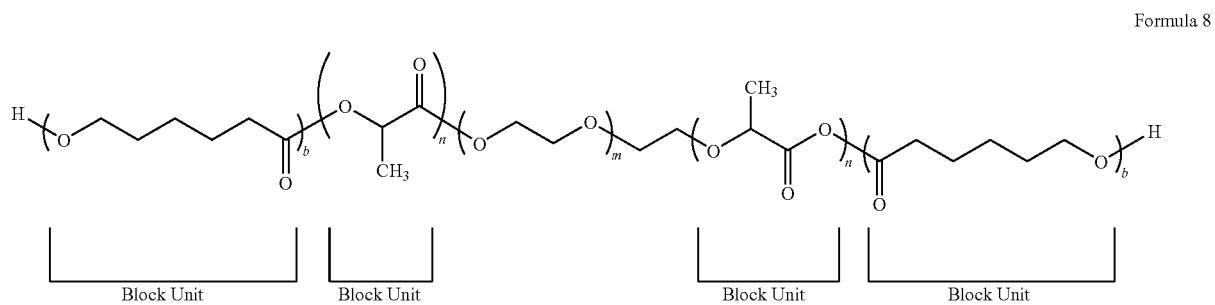

Formula 8 wherein b is an integer from about 2 to about 30,000, m is an integer from about 2 to about 30,000, and n is an integer from about 2 to about 30,000.

In another embodiment, the block copolymer further comprises a coupling group selected from the group consisting of PEG-diacids, terminal isocyanates, terminal isothiocyanates, terminal esters, terminal acid chlorides, terminal anhydrides, and combinations thereof.

In another embodiment of the present invention, the block copolymer comprises the general structure of Formula 9.

Formula 9

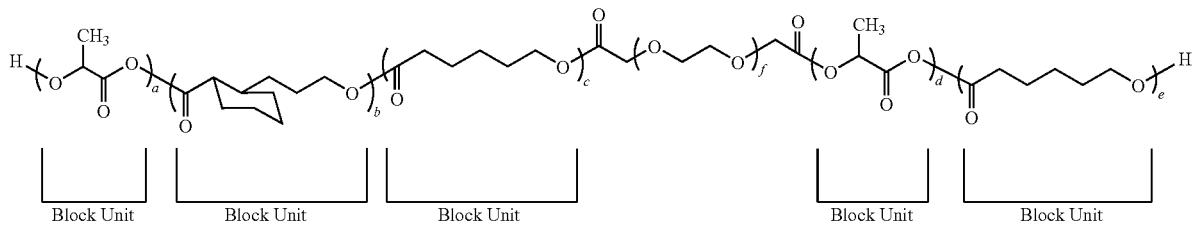

wherein a is an integer from about 2 to about 30,000, b is an integer from about 2 to about 30,000, c is an integer from about 2 to about 30,000, d is an integer from about 2 to about 30,000, e is an integer from about 2 to about 30,000, and f is an integer from about 0 to about 20.

In another embodiment of the present invention, the block copolymer comprises the general structure of Formula 11;

Formula 11

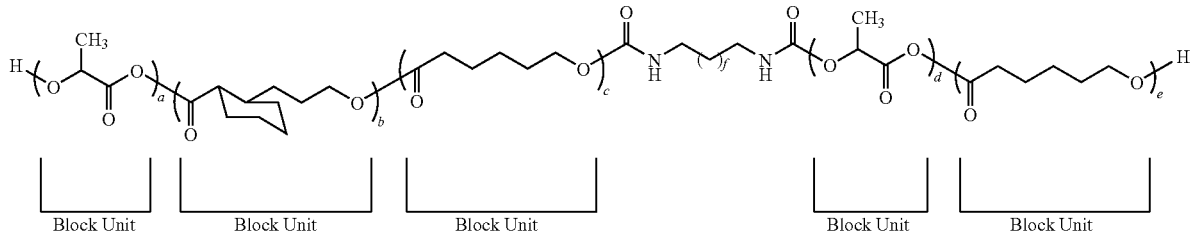

wherein a is an integer from about 2 to about 30,000, b is an integer from about 2 to about 30,000, c is an integer from about 2 to about 30,000, d is an integer from about 2 to about 30,000, e is an integer from about 2 to about 30,000, and f is an integer from about 0 to about 20.

In another embodiment, the at least one drug is selected from the group consisting of anti-proliferatives, estrogens, chaperone inhibitors, protease inhibitors, protein-tyrosine kinase inhibitors, leptomycin B, peroxisome proliferator-activated receptor gamma ligands (PPARγ), hypothemycin, nitric oxide, bisphosphonates, epidermal growth factor inhibitors, antibodies, proteasome inhibitors, antibiotics, anti-inflammatories, anti-sense nucleotides and transforming nucleic acids.

DEFINITION OF TERMS

Lactide: As used herein, "lactide" or refers to 3,6-dimethyl-1,4-dioxane. The term "DLLA" refers to either the D or L form of lactide while the term "LLA" refers to the L form of lactide. More commonly lactide is also referred to herein as the heterodimer of R and S forms of lactic acid, the homodimer of the S form of lactic acid and the homodimer of the R form of lactic acid. Lactide is also depicted below in Formula 1. Lactic acid and lactide are used interchangeably herein. The term dimer is well known to those of ordinary skill in the art.

Formula 1

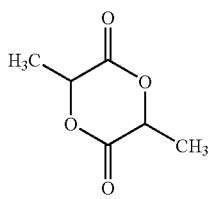

Glycolide: As used herein, "glycolide" refers to a molecule having the structure of Formula 2.

Formula 2

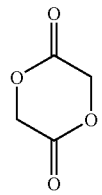

4-tert-butyl caprolactone: As used herein, "4-tert-butyl caprolactone" refers to a molecule having the structure of Formula 3.

Formula 3

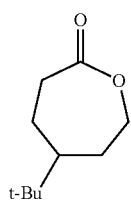

N-acetyl caprolactone: As used herein, "N-acetyl caprolactone" refers to a molecule having the structure of Formula 4.

Formula 4

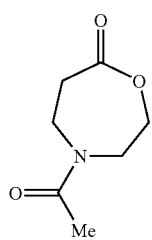

Cyclohexyl caprolactone: As used herein, "cyclohexyl caprolactone" or CCL refers to a molecule having the structures of Formula 5a-5d. As used herein "cyclohexyl caprolactone" refers to anyone of the structures of Formula 5 as well as combinations of two or more of the structures of Formula 5.

Formula 5

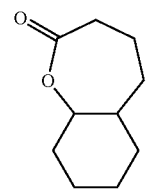

5a

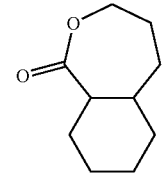

5b

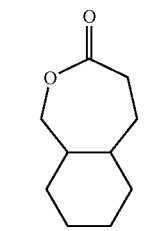

5c

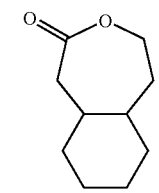

5d

Block copolymer: As used herein, "block copolymer" refers to a macromolecule composed of block (a portion of a macromolecule comprising many constitutional units [an atom or group of atoms, including pendant atoms or groups, if any]) comprising a part of the essential structure of a macromolecule, that has at least one feature which is not present in the adjacent portions wherein said "blocks" are arranged in a linear sequence.

Backbone: As used herein, "backbone" refers to the main chain of a polymer or copolymer of the present invention. A "polyester backbone" as used herein refers to the main chain of a biodegradable polymer comprising ester linkages. A "polyether backbone" as used herein refers to the main chain of a polymer comprising ether linkages. An exemplary polyether is polyethylene glycol (PEG).

Bioactive Agent(s): As used herein, "bioactive agent" shall include any compound or drug having a therapeutic effect in an animal. Exemplary, non limiting examples include anti-proliferatives including, but not limited to, macrolide antibiotics including FKBP-12 binding compounds, estrogens, chaperone inhibitors, protease inhibitors, protein-tyrosine kinase inhibitors, leptomycin B, peroxisome proliferator-activated receptor gamma ligands (PPARγ), hypothemycin, nitric oxide, bisphosphonates, epidermal growth factor inhibitors, antibodies, proteasome inhibitors, antibiotics, anti-inflammatories, anti-sense nucleotides and transforming nucleic acids. Drugs can also refer to bioactive agents including anti-proliferative compounds, cytostatic compounds, toxic compounds, anti-inflammatory compounds, chemotherapeutic agents, analgesics, antibiotics, protease inhibitors, statins, nucleic acids, polypeptides, growth factors and delivery vectors including recombinant micro-organisms, liposomes, and the like.

Exemplary FKBP-12 binding agents include sirolimus (rapamycin), tacrolimus (FK506), everolimus (certican or RAD-001), temsirolimus (CCI-779 or amorphous rapamycin 42-ester with 3-hydroxy-2-(hydroxymethyl)-2-methylpropionic acid as disclosed in U.S. patent application Ser. No. 10/930,487) and zotarolimus (ABT-578; see U.S. Pat. Nos. 6,015,815 and 6,329,386). Additionally, and other rapamycin hydroxyesters as disclosed in U.S. Pat. No. 5,362,718 may be used in combination with the polymers of the present invention.

Biocompatible: As used herein "biocompatible" shall mean any material that does not cause injury or death to the animal or induce an adverse reaction in an animal when placed in intimate contact with the animal's tissues. Adverse reactions include inflammation, infection, fibrotic tissue formation, cell death, or thrombosis.

Biodegradable: As used herein, "biodegradable" refers to a polymeric composition that is biocompatible and subject to being broken down in vivo through the action of normal biochemical pathways. From time-to-time bioresorbable and biodegradable may be used interchangeably, however they are not coextensive. Biodegradable polymers may or may not be reabsorbed into surrounding tissues, however all bioresorbable polymers are considered biodegradable. The biodegradable polymers of the present invention are capable of being cleaved into biocompatible byproducts through chemical- or enzyme-catalyzed hydrolysis.

Copolymer: As used herein, a "copolymer" is a macromolecule produced by the simultaneous or step-wise polymerization of two or more dissimilar units such as monomers. Copolymers include bipolymers (two dissimilar units), terpolymers (three dissimilar units), etc.

Controlled release: As used herein, "controlled release" refers to the release of a bioactive compound from a medical device surface at a predetermined rate. Controlled release implies that the bioactive compound does not come off the medical device surface sporadically in an unpredictable fashion and does not "burst" off of the device upon contact with a biological environment (also referred to herein a first order kinetics) unless specifically intended to do so. However, the term "controlled release" as used herein does not preclude a "burst phenomenon" associated with deployment. In some embodiments of the present invention an initial burst of drug may be desirable followed by a more gradual release thereafter. The release rate may be steady state (commonly referred to as "timed release" or zero order kinetics), that is the drug is released in even amounts over a predetermined time (with or without an initial burst phase) or may be a gradient release. A gradient release implies that the concentration of drug released from the device surface changes over time.

Ductility: As used herein, "ductility, or ductile" refers to a polymer attribute characterized by the polymer's resistance to fracture or cracking when folded, stressed or strained at operating temperatures. When used in reference to the polymer coating compostions of the present invention the normal operating temperature for the coating will be between room temperature and body temperature or approximately between 15° C. and 40° C. Polymer durability in a defined environment is often a function of its elasticity/ductility.

Functional Side Chain: As used herein, "functional side chain" refers to a first chemical constituent(s) typically capable of binding to a second chemical constituent(s), wherein the first chemical constituent modifies a chemical or physical characteristic of the second chemical constituent. Functional groups associated with the functional side chains include vinyl groups, hydroxyl groups, oxo groups, carboxyl groups, thiol groups, amino groups, phosphor groups and others known to those skilled in the art and as depicted in the present specification and claims.

Glass Transition Temperature: As used herein, "glass transition temperature" (Tg) refers to a temperature wherein a polymer structurally transitions from a elastic pliable state to a rigid and brittle state.

Hydrophilic: As used herein in reference to the bioactive agent, the term "hydrophilic" refers to a bioactive agent that has a solubility in water of more than 200 micrograms per milliliter.

Hydrophobic: As used herein in reference to the bioactive agent the term "hydrophobic" refers to a bioactive agent that has a solubility in water of no more than 200 micrograms per milliliter.

Polyesters: As used herein in reference to polymers, "polyesters" are polymers containing at least two ester linkages.

Polyethers: As used herein in reference to polymers, "polyethers" are polymers containing at least two ether linkages.

$M_n$: As used herein, "$M_n$" refers to number-average molecular weight. Mathematically it is represented by the following formula:

$$M_n = \Sigma_i N_i M_i / \Sigma_i N_i,$$

wherein the $N_i$ is the number of moles whose weight is $M_i$.

$M_w$: As used herein, "$M_w$" refers to weight average molecular weight that is the average weight that a given polymer may have. Mathematically it is represented by the following formula:

$$M_w = \Sigma_i N_i M_i^2 / \Sigma_i N_i M_i,$$

wherein $N_i$ is the number of molecules whose weight is $M_i$.

DETAILED DESCRIPTION OF THE INVENTION

The present invention provides controlled release biodegradable block copolymers for fabricating and coating medical devices. In particular, controlled release biodegradable block copolymers made in accordance with the teachings of the present invention are suitable for coating and fabricating vascular stents. The block copolymers can be customized to deliver bioactive agents including but not limited to hydrophilic or hydrophobic drugs and large molecules such as proteins or DNA.

Moreover, the block copolymers of the present invention comprise polyesters, polyethers, and polyurethanes. Monomers suitable for forming the block copolymers of the present invention include, but are not limited to, ∈-caprolactone (CL), polyethylene glycol (PEG), trimethylene carbonate, lactide (LLA), glycolide, terminal diols, and their derivatives.

The controlled release biodegradable block copolymers of the present invention can be synthesized to contain specific physical properties such as, but not limited to, glass transition temperature (Tg), biodegradation rates, bioactive agent elution rates, specific type of bioactive agent to be incorporated, ductility and other physical properties.

Drug elution from block copolymers depends on many factors including polymer density, the bioactive agent to be eluted, molecular nature of the polymer and Tg, among other properties. Higher Tgs, for example above 40° C., result in more brittle polymers while Tgs below body temperature (37° C.) most often result in more pliable and elastic polymers. If the Tg is around 0° C., the block copolymers become tacky. In one embodiment of the present invention, Tg can be controlled, such that the polymer elasticity and pliability can be varied as a function of temperature. The mechanical properties dictate the use of the block copolymers, for example, bioactive agent elution is slow from block copolymers that have high Tgs while faster rates of bioactive agent elution are observed with block copolymers possessing low Tgs.

The polymers of the present invention have polyester and polyether backbones and are comprised of monomers including, but not limited to, ε-caprolactone, polyethylene glycol (PEG), 1,8 octanediol, trimethylene carbonate, lactide, glycolide, terminal diols and their derivatives. The block copolymers of the present invention can be made amphiphilic by incorporating both hydrophilic and hydrophobic monomers. Therefore the amphiphilic block copolymers of the present invention are capable of delivering both hydrophobic and hydrophilic bioactive agents to a treatment site either as a coating on an implantable medical devices or as a medical device fabricated from the block copolymers.

The properties of controlled release biodegradable block copolymers of the present invention are governed by the monomers used and the reaction conditions employed in their synthesis including, but not limited to, temperature, solvent choice, reaction time and catalyst choice. Varying the monomer ratios allows the practitioner to fine tune, or modify, the properties of the polymer to control physical properties.

In one embodiment of the present invention, a medical device is manufactured from a biodegradable controlled release block copolymer of the present invention. In another embodiment, the biodegradable controlled release block copolymer is provided as a coating on a medical device. In yet another embodiment, the biodegradable controlled release block copolymer medical device or coating further comprises at least one bioactive agent. In one embodiment, the implantable medical device includes, but is not limited to, vascular stents, stent grafts, urethral stents, bile duct stents, catheters, guide wires, pacemaker leads, bone screws, sutures and prosthetic heart valves.

Bioactive agents suitable for controlled release from the block copolymers of the present invention include, but are not limited to, anti-proliferatives, estrogens, chaperone inhibitors, protease inhibitors, protein-tyrosine kinase inhibitors, leptomycin B, peroxisome proliferator-activated receptor gamma ligands (PPARγ), hypothemycin, nitric oxide, bisphosphonates, epidermal growth factor inhibitors, antibodies, proteasome inhibitors, antibiotics, anti-inflammatories, anti-sense nucleotides and transforming nucleic acids. Exemplary FKBP-12 binding agents include sirolimus (rapamycin), tacrolimus (FK506), everolimus (certican or RAD-001), zotarolimus (ABT-578; see U.S. Pat. Nos. 6,015,815 and 6,329,386), rapamycin 42-ester with 3-hydroxy-2-(hydroxymethyl)-2-methylpropionic acid (either amorphous or crystalline; temsirolimus (CCI-779)), as disclosed in U.S. patent application Ser. No. 10/930,487 and other rapamycin hydroxyesters as disclosed in U.S. Pat. No. 5,362,718. The entire contents of all of preceding patents and patent applications are herein incorporated by reference for all they teach related to FKBP-12 binding compounds and their derivatives.

The controlled release biodegradable block copolymers of the present invention are at least di-block polymers. The block segments of the polymers of the present invention comprise homopolymers or heteropolymers. When referring to a di-block polymer, the polymer comprises two different homopolymers or heteropolymers, a tri-block polymer comprises three different homopolymers or heteropolymers and so on. The blocks may vary in length and can vary in repeat sequence. The individual blocks will be represented herein with capital letters wherein different letters characterize different blocks. For example a di-block polymer is represented by the non-limiting sequences whereby the individual blocks are designated A or B, -[AB]-, -[AB]-[AB]-, -[AA]-[BB]-, -[AB]-[BA]-, -[AABB]-[BBAA]-[B]-[A]-, and many other configurations and combinations thereof. A tri-block polymer will further incorporate a block designated as C, a tetra-block polymer will incorporate a block designated as D and so on.

As discussed above individual blocks include heteropolymers. These heteropolymers comprise polymers with at least two different monomers. The heteropolymers can also include block copolymers as defined above.

Some block copolymers are linear, in which the blocks are connected end-to-end; however, it is possible to form other types of block-copolymers including star copolymers (also known as dendritic copolymers), in which all of the blocks are connected via one of their ends at least a single junction. More complicated arrangements are also possible. The number of monomer types in a block copolymer may be less than or equal to the number of blocks. Thus, an ABC linear tri-block consists of three monomer types, whereas an ABA linear tri-block consists of two monomer types.

One non limiting method for altering the drug elution profile of a polymer coating is to mix different block polymer components in different ratios. For example, mixtures of different polymers and/or copolymers having differing hydrophilicities and hydrophobicities can significantly affect the coating's performance. Polymer blends, however, can be difficult to make compatible and in some circumstances polymer blends can be non-uniform, resulting in inconsistent bioactive agent elution profiles. Another method for tuning a polymer/block copolymer (as used herein polymer tuning refers to a process of adjusting a polymer's composition to achieve a desired elution profile and other physical characteristics) is to alter the individual monomers that comprise a given polymer or block copolymer. Thus polymer scientists have experimented using condensation and addition techniques to tune specific polymers. While condensation and addition techniques are useful with relative simple polymers, more complex polymer structures are difficult to achieve using these methods. This is especially true when polymers are used in biomedical applications where the multi-factorial demands on a polymer's performance are critical. Thus, for the reasons already described, the present inventors turned to block copolymers as a possible alternatives to polymer coatings derived from blending a limited number of miscible polymers and copolymers and/or being limited to the few existing block copolymers made using the teachings of the prior art such as those disclosed in U.S. Pat. No. 6,855,770 which is incorporated herein by reference for all it contains regarding block copolymers. Methods are needed that permitted the use of a wider range of monomer subunits, combinations of polymers and bioactive agents and more production friendly manufacturing techniques.

The methods of synthesis of the block copolymers of the present invention include standard methods known to persons of ordinary skill in the art. In one embodiment of the present invention, the block copolymers are synthesized by forming a block from one set of monomers, and upon completion of the reaction, another set of monomers are added to provide a di-block polymer. Multi-block polymers can be synthesized with the process discussed above. This process allows for control of the molecular weight of the blocks as well as the total molecular weight of the completed polymer. In addition, the above process allows for the strategic choices of monomers that allow for optimizing the physical properties of the controlled release biodegradable block copolymers of the present invention for their intended purpose.

In one embodiment of the present invention, the controlled release biodegradable block polymer is a tri-block polymer comprising the monomers lactide, cyclohexyl caprolacotone, and caprolactone according to Formula 6 wherein a is an integer from about 2 to about 30,000, b is an integer from about 2 to about 30,000, and c is an integer from about 2 to about 30,000. In additional embodiments, a is an integer ranging from 10 to 20,000; from 20 to 10,000; from 100 to 5,000; from 200 to 4,000; from 300 to 3,000; from 400 to 2,000; or from 500 to 1000. In additional embodiments, b is an integer ranging from 10 to 20,000; from 20 to 10,000; from 100 to 5,000; from 200 to 4,000; from 300 to 3,000; from 400 to 2,000; or from 500 to 1000. In additional embodiments, c is an integer ranging from 10 to 20,000; from 20 to 10,000; from 100 to 5,000; from 200 to 4,000; from 300 to 3,000; from 400 to 2,000; or from 500 to 1000.

In another embodiment of the present invention, the controlled release biodegradable block polymer is a tri-block polymer comprising the monomers PEG, lactide, and caprolactone according to Formula 8 wherein b is an integer from about 2 to about 30,000, m is an integer from about 2 to about 30,000, and n is an integer from about 2 to about 30,000. In additional embodiments, b is an integer ranging from 10 to 20,000; from 20 to 10,000; from 100 to 5,000; from 200 to 4,000; from 300 to 3,000; from 400 to 2,000; or from 500 to 1000. In additional embodiments, m is an integer ranging from 10 to 20,000; from 20 to 10,000; from 100 to 5,000; from 200 to 4,000; from 300 to 3,000; from 400 to 2,000; or from 500 to 1000. In additional embodiments, n is an integer ranging from 10 to 20,000; from 20 to 10,000; from 100 to 5,000; from 200 to 4,000; from 300 to 3,000; from 400 to 2,000; or from 500 to 1000.

Formula 6

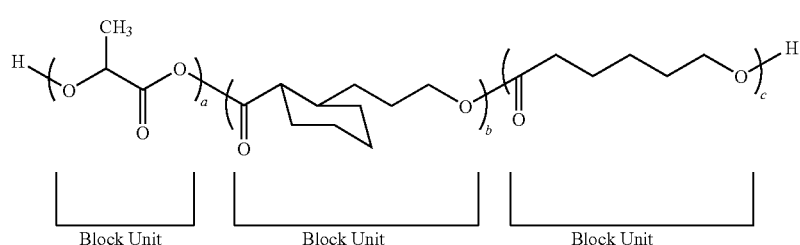

In another embodiment, the controlled release biodegradable block polymer is a di-block polymer comprising the monomers lactide and caprolactone according to Formula 7 wherein a is an integer from about 2 to about 30,000 and b is an integer from about 2 to about 30,000. In additional embodiments, a is an integer ranging from 10 to 20,000; from 20 to 10,000; from 100 to 5,000; from 200 to 4,000; from 300 to 3,000; from 400 to 2,000; or from 500 to 1000. In additional Formula 8

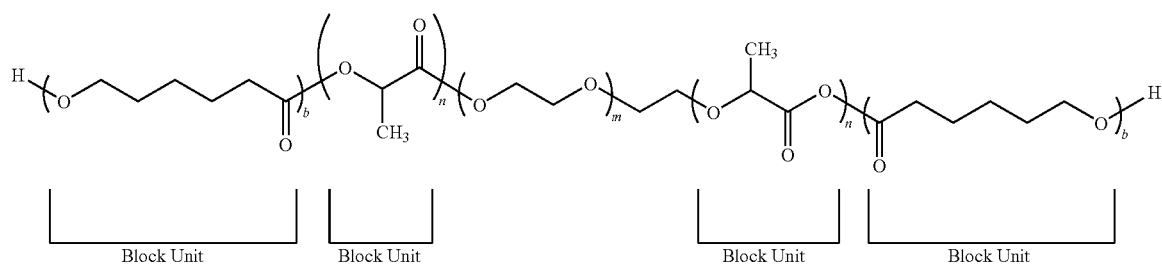

embodiments, b is an integer ranging from 10 to 20,000; from 20 to 10,000; from 100 to 5,000; from 200 to 4,000; from 300 to 3,000; from 400 to 2,000; or from 500 to 1000.

Formula 7

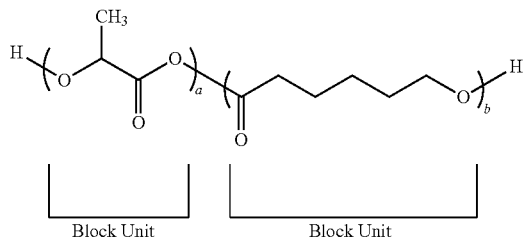

The controlled release biodegradable block copolymers of the present invention additionally comprise coupling groups. The coupling groups include, but are not limited to, PEG-diacids, terminal isocyanates, terminal isothiocyanates, terminal esters, terminal acid chlorides, terminal anhydrides, and combinations thereof.

In one embodiment of the present invention, the controlled release biodegradable block copolymer of Formula 6 is coupled to the controlled release biodegradable block copolymer of Formula 7 with a PEG diacid to produce Formula 9. In Formula 9, a is an integer from about 2 to about 30,000, b is an integer from about 2 to about 30,000, c is an integer from about 2 to about 30,000, d is an integer from about 2 to about 30,000, e is an integer from about 2 to about 30,000, and f is an integer from about 0 to about 20. In additional embodiments, a is an integer ranging from 10 to 20,000; from 20 to 10,000; from 100 to 5,000; from 200 to 4,000; from 300 to 3,000; from 400 to 2,000; or from 500 to 1000. In additional embodiments, b is an integer ranging from 10 to 20,000; from 20 to 10,000; from 100 to 5,000; from 200 to 4,000; from 300 to 3,000; from 400 to 2,000; or from 500 to 1000. In additional embodiments, c is an integer ranging from 10 to 20,000; from 20 to 10,000; from 100 to 5,000; from 200 to 4,000; from 300 to 3,000; from 400 to 2,000; or from 500 to 1000. In additional embodiments, d is an integer ranging from 10 to 20,000; from 20 to 10,000; from 100 to 5,000; from 200 to 4,000; from 300 to 3,000; from 400 to 2,000; or from 500 to 1000. In additional embodiments, e is an integer ranging from 10 to 20,000; from 20 to 10,000; from 100 to 5,000; from 200 to 4,000; from 300 to 3,000; from 400 to 2,000; or from 500 to 1000. In additional embodiments, f is an integer ranging from 2 to 18; from 4 to 16; from 6 to 14; from 8 to 12; or from 9 to 11.

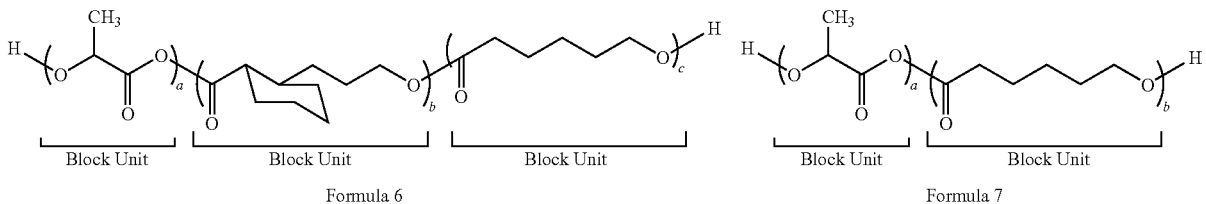

Formula 6    Formula 7

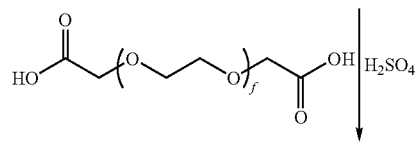

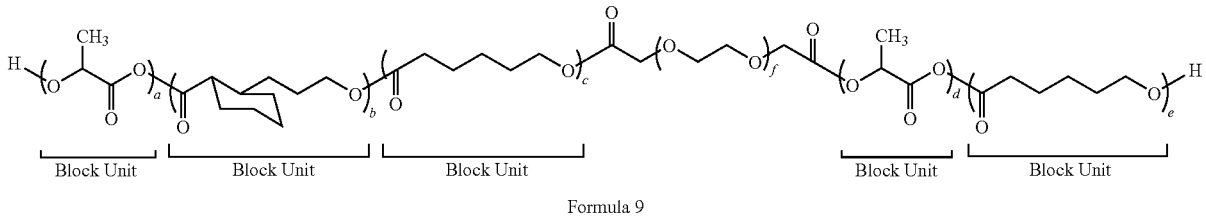

Formula 9

In another embodiment of the present invention, the controlled release biodegradable block copolymer of Formula 6 is coupled to the controlled release biodegradable block copolymer of Formula 7 with a terminal isocyanate of Formula 10 to produce Formula 11 wherein a is an integer from about 2 to about 30,000, b is an integer from about 2 to about 30,000, c is an integer from about 2 to about 30,000, d is an integer from about 2 to about 30,000, e is an integer from about 2 to about 30,000, and f is an integer from about 0 to about 6. In additional embodiments, a is an integer ranging from 10 to 20,000; from 20 to 10,000; from 100 to 5,000; from 200 to 4,000; from 300 to 3,000; from 400 to 2,000; or from 500 to 1000. In additional embodiments, b is an integer ranging from 10 to 20,000; from 20 to 10,000; from 100 to 5,000; from 200 to 4,000; from 300 to 3,000; from 400 to 2,000; or from 500 to 1000. In additional embodiments, c is an integer ranging from 10 to 20,000; from 20 to 10,000; from 100 to 5,000; from 200 to 4,000; from 300 to 3,000; from 400 to 2,000; or from 500 to 1000. In additional embodiments, d is an integer ranging from 10 to 20,000; from 20 to 10,000; from 100 to 5,000; from 200 to 4,000; from 300 to 3,000; from 400 to 2,000; or from 500 to 1000. In additional embodiments, e is an integer ranging from 10 to 20,000; from 20 to 10,000; from 100 to 5,000; from 200 to 4,000; from 300 to 3,000; from 400 to 2,000; and from 500 to 1000. In additional embodiments, f is an integer ranging from 0 to 6; from 1 to 5; or from 2 to 4.

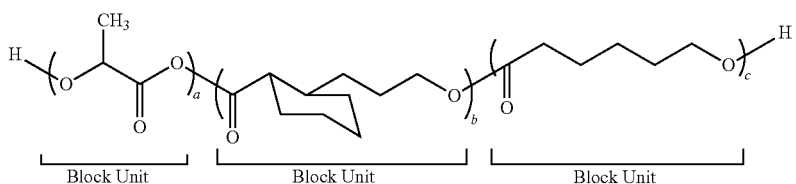

Formula 6

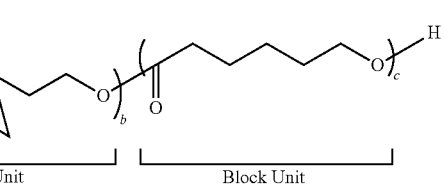

Formula 10    Formula 7

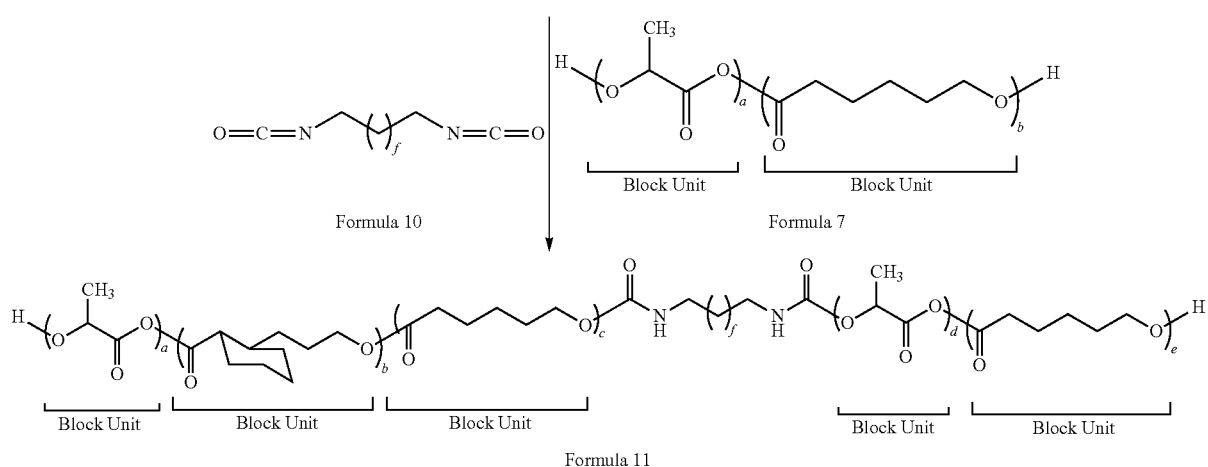

Formula 11

As discussed above, physical properties of the polymers in the present invention can be fine tuned so that the polymers can optimally perform for their intended use. Properties that can be fine tuned, without limitation, include Tg, molecular weight (both $M_n$ and MA polydispersity index (PDI, the quotient of $M_w/M_n$), degree of elasticity and degree of amphiphlicity. In one embodiment of the present invention, the Tg of the polymers is between about −10° C. to about 85° C. In still another embodiment of the present invention, the Tg of the polymers is between about 0° C. to about 70° C. In still another embodiment of the present invention, the Tg of the polymers is between about 5° C. to about 65° C. In another embodiment, the Tg of the polymers is between about 10° C. to about 60° C. In another embodiment, the Tg of the polymers is between about 15° C. to about 50° C. In another embodiment, the Tg of the polymers is between about 20° C. to about 40° C. In another embodiment, the Tg of the polymers is between about 30° C. to about 35° C. In another embodiment, the PDI of the polymers is between about 1.3 to about 4. In another embodiment, the PDI of the polymers is between about 1.5 to about 2.5.

EXAMPLES

Example 1

To a 25 mL glass serum bottle, 0.04 g of tin (II) 2-ethylhexanoate, 0.0146 g of 1,8-octanediol and 3 g of ε-caprolactone was added in a dry box. The bottle was capped and taken out of the dry box. The polymerization was carried out in an oil bath at 110° C. for 8 hrs. Then the bottle was brought back into the dry box and 7 g of lactide was added into the bottle, the bottle was resealed and then taken out of the dry box. The reaction was continued at 110° C. for an additional 12 hrs before being stopped by adding a few drops of methanol. The crude product was dissolved in chloroform, precipitated in methanol twice, collected and dried in vacuum oven to form Polymer 4 (Table 1).

Example 2

To a 25 mL glass serum bottle, 0.04 g of tin (II) 2-ethylhexanoate, 0.0146 g of 1,8-octanediol and 3 g of cyclohexyl caprolactone is added in a dry box. The bottle is capped and taken out of the dry box. The polymerization is carried out in an oil bath at 110° C. for 8 hrs. Then the bottle is brought back into the dry box and 7 g of lactide is added into the bottle, the bottle is resealed and then taken out of the dry box. The reaction is continued at 110° C. for an additional 12 hrs before being stopped by adding a few drops of methanol. The crude product is dissolved in chloroform, precipitated in methanol twice, collected and dried in vacuum oven.

Example 3

To a 25 mL glass serum bottle, 0.04 g of tin (II) 2-ethylhexanoate, 0.0146 g of 1,8-octanediol and 3 g of glycolide is added in a dry box. The bottle is capped and taken out of the dry box. The polymerization is carried out in an oil bath at 110° C. for 8 hrs. Then the bottle is brought back into the dry box and 7 g of lactide is added into the bottle, the bottle is resealed and then taken out of the dry box. The reaction is continued at 110° C. for an additional 12 hrs before being stopped by adding a few drops of methanol. The crude product is dissolved in chloroform, precipitated in methanol twice, collected and dried in vacuum oven.

Example 4

To a 25 mL glass serum bottle, 0.04 g of tin (II) 2-ethylhexanoate, 0.0146 g of 1,8-octanediol and 0.5 g of ε-caprolactone was added in a dry box. The bottle was capped and taken out of the dry box. The polymerization was carried out in an oil bath at 110° C. for 8 hrs. Then the bottle was brought back into the dry box and 9 g of lactide was added into the bottle, the bottle was resealed and then taken out of the dry box. The reaction was continued at 110° C. for an additional 12 hrs. Then the bottle was brought back into the dry box and 0.5 g of cyclohexyl caprolactone was added into the bottle. The reaction was continued at 110° C. for an additional 12 hrs before being stopped by adding a few drops of methanol. The crude product was dissolved in chloroform, precipitated in methanol twice, collected and dried in vacuum oven to form Polymer D169 (Table 1). The mechanical properties of polymer D169 are presented in Table 2.

fabricated from polymer materials that have been pelletized then dried. The dried polymer pellets are then extruded forming a coarse monofilament which is quenched. The extruded, quenched, crude monofilament is then drawn into a final monofilament with an average diameter from approximately 0.01 mm to 0.6 mm, preferably between approximately 0.05 mm and 0.15 mm. Approximately 10 to approximately 50 of the final monofilaments are then woven in a plaited fashion with a braid angle about 90 to 170 degrees on a braid mandrel sized appropriately for the application. The plaited stent is then removed from the braid mandrel and disposed onto an annealing mandrel having an outer diameter of equal to or less than the braid mandrel diameter and annealed at a tempera-

TABLE 1

| Polymer | Monomers | Feeding ratio (mass) | Feeding ratio (mole) | Final composition $^1$H NMR | $M_n$ (g/mol) | PDI | Tg (° C.) | Tm (° C.) |
|---|---|---|---|---|---|---|---|---|
| 169 | lactide/cyclohexyl caprolactone/caprolactone | 90/5/5 | 90.6/5.1/4.3 | 90/10* | 8900 | 1.66 | 33.29 | 141.5 |
| 170 | lactide/caprolactone | 90/10 | 87.7/12.3 | 88.5/11.5 | 10300 | 1.57 | 20.17 | 140.82 |
| 177 | lactide/caprolactone | 80/20 | 83.4/16.5 | 76.8/23.2 | 4160 | 1.37 | 27.71 | 152.70 |
| 178 | lactide/caprolactone | 70/30 | 64.9/35.1 | 64.8/35.2 | 7536 | 1.50 | ND* | 155.72 |
| 179 | lactide/caprolactone | 90/10 | 84/16 | 87.2/12.8 | 272000 | 1.73 | 59.62 | 174.36 |
| 180 | lactide/caprolactone | 80/20 | 83.4/16.5 | 65.9/34.1 | 260000 | 1.59 | 60.11 | 174.51 |
| 184 | lactide/caprolactone | 70/30 | 64.9/35.1 | 65.5/34.5 | 21940 | 1.91 | | 171.52 |
| D12 | PEG3400/DLLA/CL | 0.5/10/2 | 1.47/694/176 | 0.1/84.6/15.3 | 28704 | 1.58 | 24.2-25.6 | ND |
|  | PEG3400/DLLA/LLA/CL | 0.5/8/2/2.5 | 1.47/556/139/220 | 0.2/82.0/17.9 | 25203 | 1.68 | 16.9-17.8 | ND |

ND = not determined
*can not differentiate CCL and CL in final product from $^1$H NMR, 10% is the total percentage of CCL and CL.

TABLE 2

| Modulus (Mpa) | 876 |
|---|---|
| Break Strain (%) | 282.5 |
| Yield Strain (%) | 5.7 |
| Ultimate Stress (Mpa) | 49.7 |
| Yield Stress | 44.1 |

Mpa = megapascal

However, persons having ordinary skill in the art of polymer chemistry will immediately realize that the method disclosed in Example 4 is appropriate for the synthesis of any polymer disclosed in Table 1. Table 1 presents feeding ratios (mass) as well as other information required to adjust the general parameters in Example 4 to embrace all polymers comprising poly(LLA-b-CL-b-LLA) blocks.

Exemplary block copolymers of the present invention with their associated characterization data are presented in Table 1. The monomer feeding ratios are detailed and $^1$H NMR studies of the polymers provide the final monomer composition of the polymers. Standard techniques such as differential scanning calorimetry and gel permeation chromatography are used to measure $M_n$, PDI, Tg and Tm.

For exemplary, non-limiting, purposes a vascular stent will be described. A controlled release biodegradable block copolymers is heated until molten in the barrel of an injection molding machine and forced into a stent mold under pressure. After the molded polymer (which now resembles and is a stent) is cooled and solidified the stent is removed from the mold. In one embodiment of the present invention the stent is a tubular shaped member having first and second ends and a walled surface disposed between the first and second ends. The walls are composed of extruded polymer monofilaments woven into a braid-like embodiment. In the second embodiment, the stent is injection molded or extruded. Fenestrations are molded, laser cut, die cut, or machined in the wall of the tube. In the braided stent embodiment monofilaments are ture between about the polymer glass transition temperature and the melting temperature of the polymer blend for a time period between about five minutes and about 18 hours in air, an inert atmosphere or under vacuum. The stent is then allowed to cool and is then cut.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on the described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. An implantable medical device comprising a controlled release biodegradable block copolymer and at least one drug releasable from said controlled release biodegradable block copolymer; wherein said controlled release biodegradable block copolymer comprises at least two block copolymers coupled together by a coupling group;
wherein at least one block copolymer comprises Formula 7

Formula 7

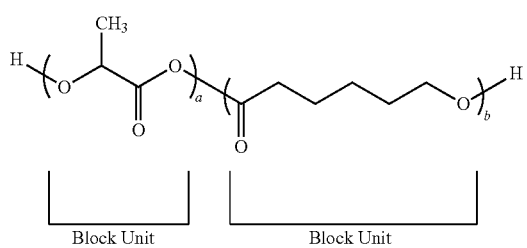

wherein a is an integer from about 100 to about 30,000 and b is an integer from about 100 to about 30,000; and
wherein said coupling group is selected from the group consisting of PEG-diacids, terminal isocyanates, terminal isothiocyanates, terminal esters, terminal acid chlorides, terminal anhydrides, and combinations thereof.

2. An implantable medical device having a controlled release coating thereon wherein said coating comprises a controlled release biodegradable block copolymer and at least one drug releasable from said biodegradable block copolymer; wherein said biodegradable block copolymer comprises at least two block copolymers coupled together by a coupling group;
wherein at least one block copolymer comprises Formula 7

Formula 7

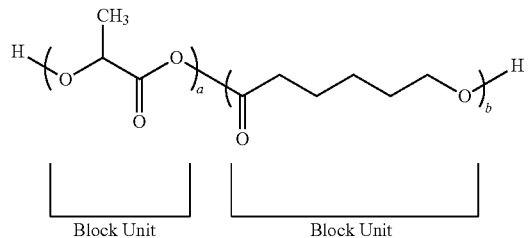

wherein a is an integer from about 100 to about 30,000 and b is an integer from about 100 to about 30,000; and
wherein said coupling group is selected from the group consisting of PEG-diacids, terminal isocyanates, terminal isothiocyanates, terminal esters, terminal acid chlorides, terminal anhydrides, and combinations thereof.

3. The implantable medical device of claim 1 wherein said medical device is a vascular stent.

4. The implantable medical device according to claim 1 wherein said at least one drug is selected from the group consisting of anti-proliferatives, estrogens, chaperone inhibitors, protease inhibitors, protein-tyrosine kinase inhibitors, leptomycin B, peroxisome proliferator-activated receptor gamma ligands (PPARγ), hypothemycin, nitric oxide, bisphosphonates, epidermal growth factor inhibitors, antibodies, proteasome inhibitors, antibiotics, anti-inflammatories, and anti-sense nucleotides.

5. The implantable medical device according to claim 1 wherein said drug comprises at least one compound selected from the group consisting of sirolimus (rapamycin), tacrolimus (FK506), everolimus (certican), temsirolimus (CCI-779) and zotarolimus (ABT-578).

6. The implantable medical device of claim 2 wherein said medical device is a vascular stent.

7. The implantable medical device according to claim 2 wherein said at least one drug is selected from the group consisting of anti-proliferatives, estrogens, chaperone inhibitors, protease inhibitors, protein-tyrosine kinase inhibitors, leptomycin B, peroxisome proliferator-activated receptor gamma ligands (PPARγ), hypothemycin, nitric oxide, bisphosphonates, epidermal growth factor inhibitors, antibodies, proteasome inhibitors, antibiotics, anti-inflammatories, and anti-sense nucleotides.

8. The implantable medical device according to claim 2 wherein said drug comprises at least one compound selected from the group consisting of sirolimus (rapamycin), tacrolimus (FK506), everolimus (certican), temsirolimus (CCI-779) and zotarolimus (ABT-578).

9. The implantable medical device according to claim 1 wherein at least one block copolymer comprises Formula 6

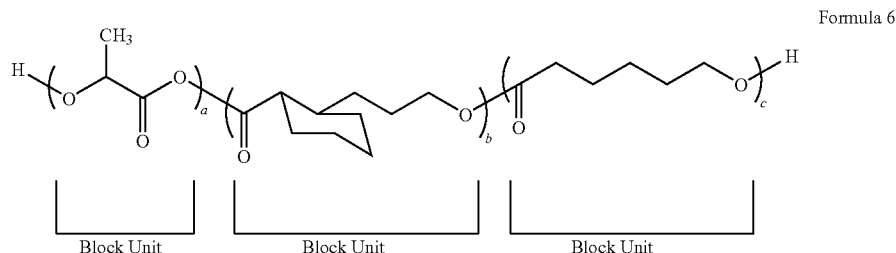

Formula 6 wherein a is an integer from about 2 to about 30,000, b is an integer from about 2 to about 30,000, and c is an integer from about 2 to about 30,000.

10. The implantable medical device according to claim 2 wherein at least one block copolymer comprises Formula 6

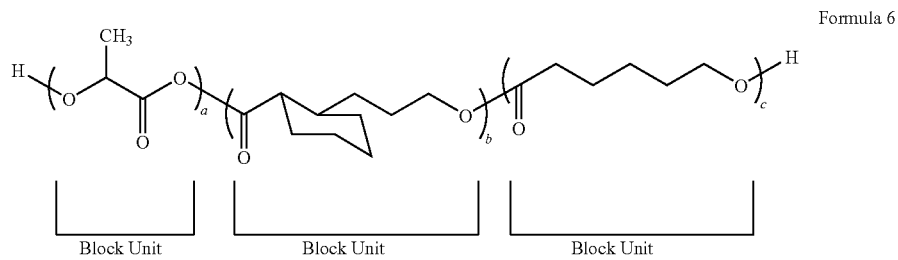

Formula 6 wherein a is an integer from about 2 to about 30,000, b is an integer from about 2 to about 30,000, and c is an integer from about 2 to about 30,000.

11. The implantable medical device according to claim 1 wherein the block copolymer of Formula 7 is prepared from 70-90 wt-% lactide and 10-30 wt-% caprolactone.

12. The implantable medical device according to claim 2 wherein the block copolymer of Formula 7 is prepared from 70-90 wt-% lactide and 10-30 wt-% caprolactone.

13. The implantable medical device according to claim 1 wherein in the block copolymer of Formula 7, a is an integer from about 100 to about 5000 and b is an integer from about 100 to about 5000.

14. The implantable medical device according to claim 2 wherein in the block copolymer of Formula 7, a is an integer from about 100 to about 5000 and b is an integer from about 100 to about 5000.

* * * * *